United States Patent
Roorda et al.

(10) Patent No.: US 10,525,248 B2
(45) Date of Patent: Jan. 7, 2020

(54) APPARATUS AND METHOD FOR PROMOTING FLUID UPTAKE INTO AN IMPLANT

(71) Applicant: Nano Precision Medical, Inc., Emeryville, CA (US)

(72) Inventors: Wouter E. Roorda, Emeryville, CA (US); William G. M. Fischer, Emeryville, CA (US); Kathleen Fischer, Emeryville, CA (US); Adam D. Mendelsohn, Emeryville, CA (US); Adam Monkowski, Emeryville, CA (US)

(73) Assignee: NANO PRECISION MEDICAL, INC., Emeryville, CA (US)

( * ) Notice: Subject to any disclaimer, the term of this patent is extended or adjusted under 35 U.S.C. 154(b) by 0 days.

(21) Appl. No.: 15/419,487

(22) Filed: Jan. 30, 2017

(65) Prior Publication Data
US 2017/0136224 A1    May 18, 2017

Related U.S. Application Data

(63) Continuation of application No. PCT/US2016/014750, filed on Jan. 25, 2016.
(Continued)

(51) Int. Cl.
*A61M 39/02* (2006.01)
*A61M 37/00* (2006.01)
*A61K 9/00* (2006.01)

(52) U.S. Cl.
CPC .... *A61M 39/0208* (2013.01); *A61M 37/0069* (2013.01); *A61K 9/0024* (2013.01); *A61M 2039/0205* (2013.01)

(58) Field of Classification Search
CPC .......... A61M 39/0208; A61M 37/0069; A61K 9/0024; A61K 9/22
See application file for complete search history.

(56) References Cited

U.S. PATENT DOCUMENTS

| 3,324,854 A | 6/1967 | Weese |
| 4,994,028 A * | 2/1991 | Leonard ............ A61M 37/0069 604/59 |

(Continued)

FOREIGN PATENT DOCUMENTS

| EP | 0 596 161 A1 | 9/2014 |
| WO | 98/13091 A1 | 4/1998 |

(Continued)

OTHER PUBLICATIONS

International Patent Application No. PCT/US2016/014750, International Search Report, dated Jun. 10, 2016, 5 pages.
(Continued)

*Primary Examiner* — Nathan R Price
*Assistant Examiner* — Tasnim Mehjabin Ahmed
(74) *Attorney, Agent, or Firm* — Kilpatrick Townsend & Stockton LLP

(57) ABSTRACT

The invention pertains to apparatuses, means and methods to promote uptake of fluids into a reservoir of an implantable drug delivery system though a porous membrane. Embodiments of the invention promote fluid uptake by creating a pressure differential between the reservoir of the drug delivery device and the environment of the device after implantation, for instance a subcutaneous pocket.

18 Claims, 10 Drawing Sheets

Related U.S. Application Data

(60) Provisional application No. 62/107,912, filed on Jan. 26, 2015.

(56) References Cited

U.S. PATENT DOCUMENTS

| | | | |
|---|---|---|---|
| 5,167,622 A | 12/1992 | Muto | |
| 7,056,300 B2 | 6/2006 | Alexandre et al. | |
| 8,603,051 B2 | 12/2013 | Kuo et al. | |
| 2002/0111603 A1* | 8/2002 | Cheikh | A61D 7/00 |
| | | | 604/891.1 |
| 2003/0233101 A1* | 12/2003 | Lubock | A61M 37/0069 |
| | | | 606/116 |
| 2005/0101967 A1* | 5/2005 | Weber | A61F 2/167 |
| | | | 606/107 |
| 2010/0036465 A1 | 2/2010 | Glukhovsky et al. | |
| 2011/0106006 A1 | 5/2011 | Martin et al. | |
| 2011/0184449 A1 | 7/2011 | Lubock et al. | |
| 2013/0237910 A1* | 9/2013 | Shetty | A61M 37/0069 |
| | | | 604/110 |

FOREIGN PATENT DOCUMENTS

| | | | |
|---|---|---|---|
| WO | 2011/112916 A1 | 9/2011 | |
| WO | WO-2013085951 A1 * | 6/2013 | C25D 11/26 |
| WO | 2014/137901 A1 | 9/2014 | |

OTHER PUBLICATIONS

International Search Report and Written Opinion dated Jun. 10, 2016 for PCT/US2016/014750 filed Jan. 25, 2016, 14 pages.

* cited by examiner

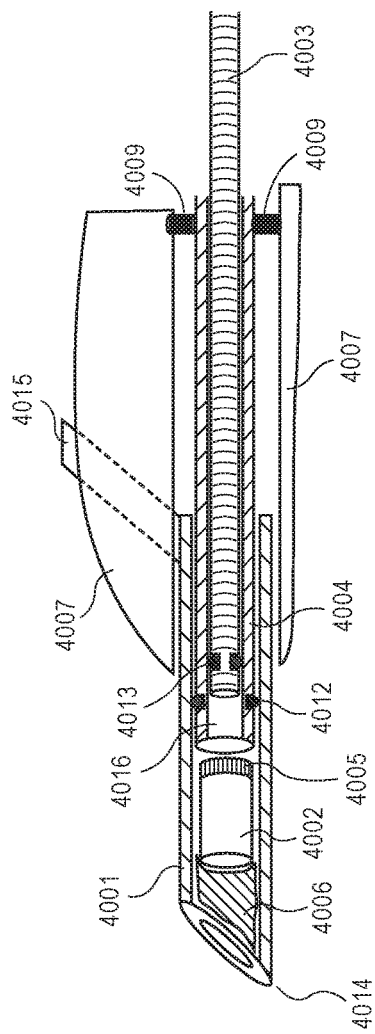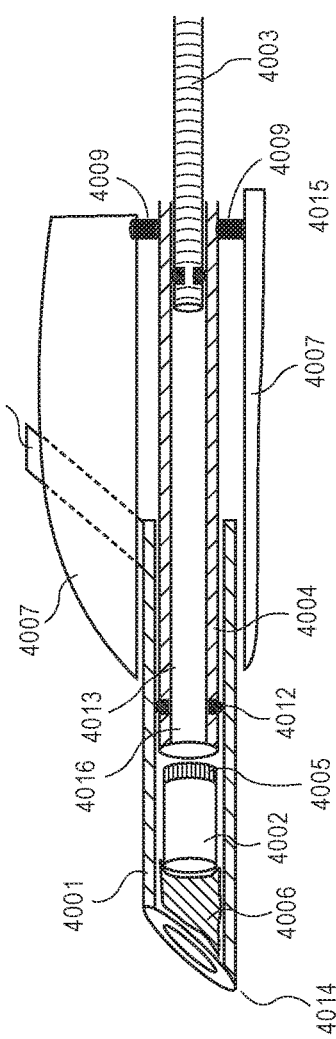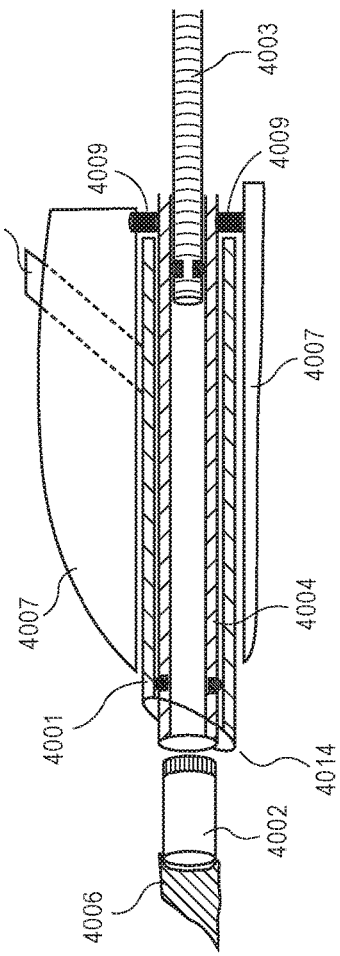

APPARATUS AND METHOD FOR PROMOTING FLUID UPTAKE INTO AN IMPLANT

CROSS-REFERENCE TO RELATED APPLICATIONS

The present application is a Continuation of PCT/US2016/014750 filed Jan. 25, 2016; which claims priority to U.S. Provisional Application No. 62/107,912 filed Jan. 26, 2015, the teachings of which are hereby incorporated by reference in their entirety for all purposes.

BACKGROUND OF THE INVENTION

Many beneficial substances, including many therapeutic agents, require long-term delivery to a target site of action to be optimally effective. Well-known examples include drugs that need to be administered for extended periods of time to a patient. Many extended release formulations have been developed for this purpose. A common issue with all of these formulations is that the drugs administered need to be stabilized in the formulation for the duration of the shelf-life of their dosage form, in addition to the stabilization required during the extended release period.

In many cases, drugs are more stable in a dry or solid formulation than in a dissolved state, hence formulations having a solid formulation during shelf life are often preferred. In some instances, the solid drug may be dispersed in a liquid, resulting in a liquid formulation comprising a solid drug. However, in order to be released from their dosage form, drugs almost always rely on some type of diffusional mechanism, which inherently requires the drugs to be in solution. Therefore, many dosage forms rely on the uptake of water after administration to a patient to bring the drugs from a solid form into solution, prior to release from the dosage form.

One type of dosage form that has been developed to address the issue of extended release of therapeutic agents is that of implantable drug delivery devices, in which a reservoir holding a drug formulation is combined with a release rate controlling mechanism, such as a release rate controlling membrane. In many instances, when a solid or dry formulation, like a powder, is filled into such a reservoir, a quantity of air is included in the reservoir. As was mentioned above, many of these dosage forms rely on the uptake of water to bring their drugs from the solid form into solution, essentially requiring that air inside the reservoir be replaced with water. Oftentimes, this will require simultaneous mass transport of water into a device and air out of the device. For those dosage forms that do not allow for such simultaneous transport, proper hydration of the formulation inside the reservoir may be impeded. One type of dosage form where this can be the case is implantable drug delivery systems having a capsule encapsulating a reservoir containing a therapeutic agent in a dry form, and a release rate controlling membrane based on nanopores. In many cases, the reservoir and the nanopores will contain an amount of air in addition to the therapeutic agent, and mass transport of interstitial fluid into the reservoir after implantation may be impeded by the presence of the air. Therefore, additional technologies are desired that allow for proper hydration in such dosage forms.

BRIEF SUMMARY OF THE INVENTION

In one embodiment, the present invention provides an apparatus for promoting fluid uptake into an implantable drug delivery device, the apparatus comprising:

a housing;
a tubular outer member extending from the housing in a distal direction;
an obturator, at least partially slideably disposed within the tubular outer member; and
a pressure reducer.

In certain instances, the pressure reducer is a slideable pressure reducer.

In certain instances, the pressure reducer is at least partially disposed within the tubular outer member.

In certain instances, the obturator is tubular, and wherein the slideable pressure reducer is at least partially disposed within the tubular obturator.

In certain instances, the pressure reducer is tubular, and wherein the slideable obturator is at least partially disposed within the tubular pressure reducer.

In certain instances, the tubular outer member is attached to the housing.

In certain instances, the tubular outer member is a slideable member, partially disposed within the housing.

In certain instances, the obturator is attached to the housing.

In certain instances, the apparatus further comprises:
a cylindrical cavity having an inner wall, the cavity being located within the housing and being connected with the tubular outer member;
wherein the slideable pressure reducer is at least partially disposed within the cylindrical cavity and comprises:
a slideable cylindrical sealing plug in sealing contact with the inner wall of the cylindrical cavity;
a handle, attached to the sealing plug and extending through the cylindrical cavity in a proximal direction; and
an aperture in the sealing disk, the obturator being disposed through the aperture, the aperture forming a sealing mechanism around the obturator.

In certain instances, the apparatus further comprises an implantable drug delivery device, the device being disposed within the tubular outer member in a location distal to the obturator and the pressure reducer, the device comprising a reservoir and a porous membrane, the membrane providing a pathway for mass transport through fluid flow between the reservoir and an environment of the drug delivery device, the membrane being in fluid contact with the pressure reducer.

In certain instances, the porous membrane is a nanoporous membrane.

In certain instances, the porous membrane is a titania nanotube membrane.

In certain instances, the apparatus further comprises a plug, disposed within the tubular outer member in a location distal to the implantable drug delivery device, the plug providing a sealing mechanism within the tubular outer member.

In certain instances, the plug is a soluble plug.

In certain instances, the plug is a biodegradable plug.

In certain instances, the apparatus further comprises a quantity of gas disposed within the tubular outer member, wherein the quantity of gas includes at least 10% by weight of one or more gases with a solubility in water at a temperature of 37° C. and a pressure of 1 atmosphere that is higher than the solubility of air in water at a temperature of 37° C. and a pressure of 1 atmosphere.

In another embodiment, the present invention provides an apparatus for promoting fluid uptake into an implantable drug delivery device, the apparatus comprising:

a housing with a distal end and a proximal end;
a tubular outer member with a distal end and a proximal end, the tubular outer member being attached to the housing towards the distal end of the housing;
a slideable obturator, at least partially disposed within the tubular outer member; and
means to reduce pressure inside the implantable drug delivery device.

In certain instances, the means comprise a slideable pressure reducer in fluid contact with the implantable drug delivery device.

In certain instances, the slideable pressure reducer is at least partially disposed within the tubular outer member.

In certain instances, the obturator is tubular, and wherein the slideable pressure reducer is at least partially disposed within the tubular obturator.

In certain instances, the pressure reducer is tubular, and wherein the slideable obturator is at least partially disposed within the tubular pressure reducer.

In certain instances, the tubular outer member is attached to the housing.

In certain instances, wherein the tubular outer member is a slideable member, partially disposed within the housing.

In certain instances, the obturator is attached to the housing.

In certain instances, the apparatus further comprises:
a cylindrical cavity having an inner wall, the cavity being located within the housing and being connected with the tubular outer member;
wherein the slideable pressure reducer is at least partially disposed within the cylindrical cavity and comprises:
a slideable cylindrical sealing plug in sealing contact with the inner wall of the cylindrical cavity;
a handle, attached to the sealing plug and extending through the cylindrical cavity in a proximal direction; and
an aperture in the sealing disk, the obturator being disposed through the aperture, the aperture forming a sealing mechanism around the obturator.

In certain instances, the apparatus further comprises the implantable drug delivery device, the device being disposed within the tubular outer member in a location distal to the obturator and the pressure reducer, the device comprising a reservoir and a porous membrane, the membrane providing a pathway for mass transport through fluid flow between the reservoir and an environment of the drug delivery device, the membrane being in fluid contact with the pressure reducer.

In certain instances, the porous membrane is a nanoporous membrane.

In certain instances, the apparatus further comprises a plug, disposed within the tubular outer member in a location distal to the implantable drug delivery device, the plug providing a sealing mechanism within the tubular outer member.

In certain instances, the plug is a soluble plug.

In certain instances, the plug is a biodegradable plug.

In certain instances, the apparatus further comprising a quantity of gas disposed within the tubular outer member, wherein the quantity of gas includes at least 10% by weight of one or more gases with a solubility in water at a temperature of 37° C. and a pressure of 1 atmosphere that is higher than the solubility of air in water at a temperature of 37° C. and a pressure of 1 atmosphere.

In one embodiment, the present invention provides a method for promoting fluid uptake into an implantable drug delivery device, the method comprising:
providing an apparatus;
the apparatus comprising:
a housing;
a tubular outer member extending from the housing in a distal direction;
an obturator, at least partially slideably disposed within the tubular outer member; and
a pressure reducer;
providing the implantable drug delivery device in a location within the tubular outer member distal to the obturator;
operating the pressure reducer to reduce pressure inside the reservoir;
introducing the implantable drug delivery device from the outer member into an environment containing a fluid; and
exposing the reservoir through the membrane to the fluid.

In certain instances, the pressure reducer is a slideable pressure reducer.

In certain instances, the pressure reducer is at least partially disposed within the tubular outer member.

In certain instances, the obturator is tubular, and wherein the slideable pressure reducer is at least partially disposed within the tubular obturator.

In certain instances, the pressure reducer is tubular, and wherein the slideable obturator is at least partially disposed within the tubular pressure reducer.

In certain instances, the tubular outer member is attached to the housing.

In certain instances, tubular outer member is a slideable member, partially disposed within the housing.

In certain instances, the obturator is attached to the housing.

In certain instances, the apparatus further comprises:
a cylindrical cavity having an inner wall, the cavity being located within the housing and being connected with the tubular outer member;
wherein the slideable pressure reducer is at least partially disposed within the cylindrical cavity and comprises:
a slideable cylindrical sealing plug in sealing contact with the inner wall of the cylindrical cavity;
a handle, attached to the sealing plug and extending through the cylindrical cavity in a proximal direction; and
an aperture in the sealing disk, the obturator being disposed through the aperture, the aperture forming a sealing mechanism around the obturator.

In certain instances, the device comprises a reservoir and a porous membrane, the membrane providing a pathway for mass transport through fluid flow between the reservoir and an environment of the drug delivery device, the membrane being in fluid contact with the pressure reducer.

In certain instances, the porous membrane is a nanoporous membrane.

In certain instances, the porous membrane is a titania nanotube membrane.

In certain instances, the apparatus further comprises a plug, disposed within the tubular outer member in a location distal to the implantable drug delivery device, the plug providing a sealing mechanism within the tubular outer member.

In certain instances, the plug is a soluble plug.

In certain instances, the plug is a biodegradable plug.

In certain instances, the apparatus further comprises a quantity of gas disposed within the tubular outer member, wherein the quantity of gas includes at least 10% by weight of one or more gases with a solubility in water at a temperature of 37° C. and a pressure of 1 atmosphere that is higher than the solubility of air in water at a temperature of 37° C. and a pressure of 1 atmosphere.

In certain instances, the pressure inside the apparatus is reduced to less than 0.5 atmosphere.

In certain instances, the pressure inside the apparatus is reduced to less than 0.1 atmosphere.

In certain instances, the pressure inside the apparatus is reduced to less than 0.01 atmosphere.

In yet another embodiment, the present invention provides an apparatus for promoting fluid uptake into an implantable drug delivery device, the apparatus comprising:
 a housing with a distal end and a proximal end;
 a tubular outer member with a distal end and a proximal end, the tubular outer member being attached to the housing towards the distal end of the housing;
 a slideable obturator, at least partially disposed within the tubular outer member; and
 a connector for connecting to a pressure reducer.

In certain instances, the connector is attached to one of the tubular outer member and the slideable obturator.

In certain instances, the apparatus further comprises the implantable drug delivery device, the device being disposed within the tubular outer member in a location distal to the obturator and the pressure reducer, the device comprising a reservoir and a porous membrane, the membrane providing a pathway for mass transport through fluid flow between the reservoir and an environment of the drug delivery device, the membrane being in fluid contact with the pressure reducer.

In certain instances, the porous membrane is a nanoporous membrane.

In certain instances, the porous membrane is a titania nanotube membrane.

In certain instances, the apparatus further comprises a plug, disposed within the tubular outer member in a location distal to the implantable drug delivery device, the plug providing a sealing mechanism within the tubular outer member.

In certain instances, the plug is a soluble plug.

In certain instances, the plug is a biodegradable plug.

In certain instances, the apparatus further comprises a quantity of gas disposed within the tubular outer member, wherein the quantity of gas includes at least 10% by weight of one or more gases with a solubility in water at a temperature of 37° C. and a pressure of 1 atmosphere that is higher than the solubility of air in water at a temperature of 37° C. and a pressure of 1 atmosphere.

In still yet another embodiment, the present invention provides an accessory unit for promoting fluid uptake into an implantable drug delivery device, the drug delivery device being disposed within a tubular outer member of an apparatus to promote fluid uptake into the drug delivery device, the accessory unit comprising:
 a first chamber having a septum suitable for accessing the first chamber with the tubular outer member and for maintaining a sealing mechanism around the tubular outer member after accessing the first chamber; and
 a second chamber, the first chamber and the second chamber being connected through a valved connector, the second chamber configured for holding liquid for uptake into the implant.

In certain instances, the implantable drug delivery device contains a formulation of a peptide or protein.

In certain instances, the protein or peptide is selected from the group consisting of beta-glucocerobrosidase, interferon alpha, interferon beta, agasidase alpha, agasidase beta, exenatide, octreotide, LHRH, LHRH analog, calcitonin, nutropin/somatropin, factor VIII, aldesleukin, forigerimod, NP fusion proteins, IL-12, a melanocyte stimulating hormone, and bapineuzumab.

In certain instances, the protein or peptide is a member selected from the group consisting of exenatide and octreotide.

In certain instances, the protein or peptide is exenatide.

In certain instances, the amount of exenatide is from about 60 µg to about 50 mg.

In certain instances, the implantable drug delivery device contains a formulation of a peptide or protein.

In certain instances, the protein or peptide is selected from the group consisting of beta-glucocerobrosidase, interferon alpha, interferon beta, agasidase alpha, agasidase beta, exenatide, octreotide, LHRH, LHRH analog, calcitonin, nutropin/somatropin, factor VIII, aldesleukin, forigerimod, NP fusion proteins, IL-12, a melanocyte stimulating hormone, and bapineuzumab.

In certain instances, the protein or peptide is a member selected from the group consisting of exenatide and octreotide.

In certain instances, the protein or peptide is exenatide.

In certain instances, the amount of exenatide is from about 60 µg to about 50 mg.

In certain instances, the implantable drug delivery device contains a formulation of a peptide or protein.

In certain instances, the protein or peptide is selected from the group consisting of beta-glucocerobrosidase, interferon alpha, interferon beta, agasidase alpha, agasidase beta, exenatide, octreotide, LHRH, LHRH analog, calcitonin, nutropin/somatropin, factor VIII, aldesleukin, forigerimod, NP fusion proteins, IL-12, a melanocyte stimulating hormone, and bapineuzumab.

In certain instances, the protein or peptide is a member selected from the group consisting of exenatide and octreotide.

In certain instances, the protein or peptide is exenatide.

In certain instances, the amount of exenatide is from about 60 µg to about 50 mg.

In certain instances, the implantable drug delivery device contains a formulation of a peptide or protein.

In certain instances, the protein or peptide is selected from the group consisting of beta-glucocerobrosidase, interferon alpha, interferon beta, agasidase alpha, agasidase beta, exenatide, octreotide, LHRH, LHRH analog, calcitonin, nutropin/somatropin, factor VIII, aldesleukin, forigerimod, NP fusion proteins, IL-12, a melanocyte stimulating hormone, and bapineuzumab.

In certain instances, the protein or peptide is a member selected from the group consisting of exenatide and octreotide.

In certain instances, the protein or peptide is exenatide.

In certain instances, the amount of exenatide is from about 60 µg to about 50 mg.

In another embodiment, the present invention provides a method to improve fluid uptake into an implantable drug delivery device, the method comprising:
 providing an implantable drug delivery device, the device comprising a reservoir and a porous membrane, the membrane providing a pathway for mass transport through fluid flow between the reservoir and an environment of the drug delivery device;

reducing pressure inside the drug delivery device prior to implantation; and implanting the device into a subject.

These and other aspects, objects and embodiments will become more apparent when read with the detailed description of the invention and the figures which follow.

BRIEF DESCRIPTION OF THE DRAWINGS

FIG. 4A-4C illustrate cross sectional side views of an embodiment of the invention in different stages of use.

DETAILED DESCRIPTION OF THE INVENTION

Definitions

Figure 1:
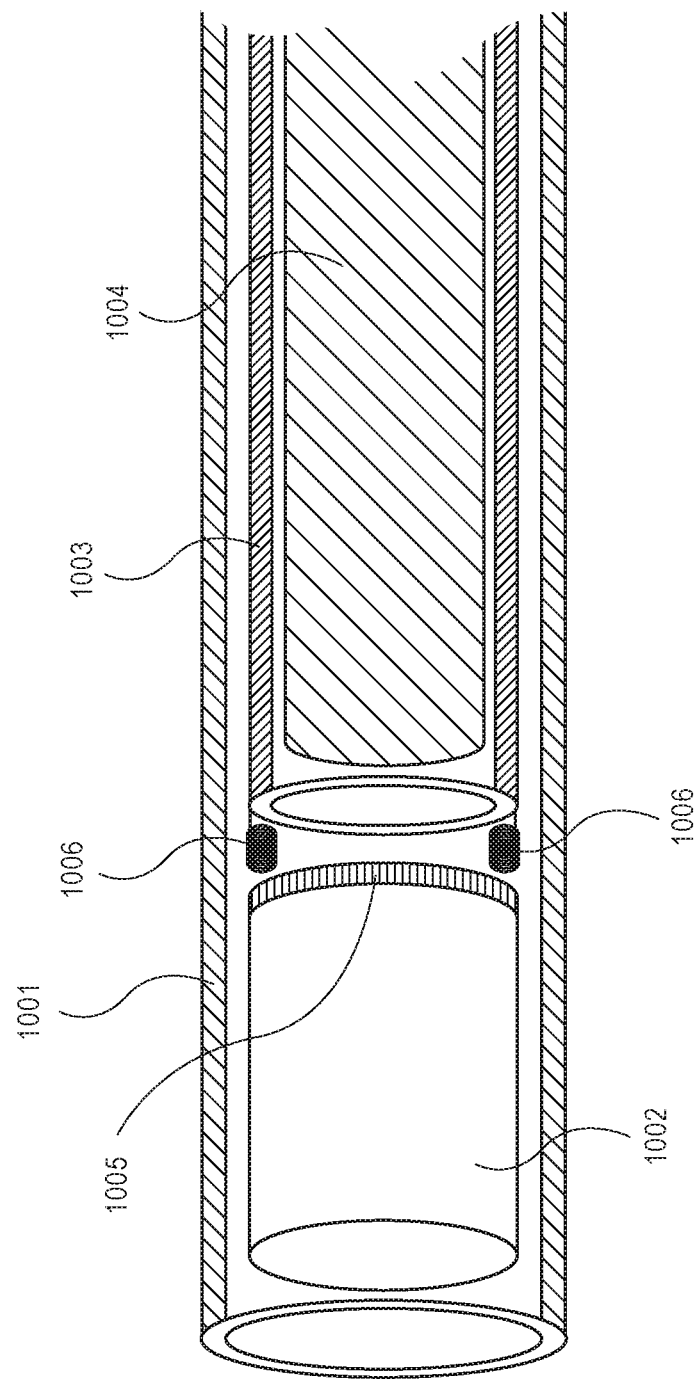
FIG. 1 illustrates a cross-sectional side view of an embodiment of the invention.

"Obturator" refers to an elongated member, suitable for moving an object within a tubular member with respect to the tubular member.

"Membrane" refers to a porous structure allowing mass transport of molecules from one side of the structure to the other through the structure.

"Porous membrane" refers to a porous structure wherein at least some of its pores are open on both ends and form fluid-filled pathways allowing for mass transport through the structure by fluid flow.

"Nanoporous membrane" refers to a porous structure wherein at least some of its pores are open on both ends and form fluid-filled pathways having a smallest dimension less than one micrometer and allowing for mass transport through the structure by fluid flow.

"Titania nanotube membrane" refers to a nanoporous membrane having an array of titania nanotubes on a titanium substrate where at least a portion of the titania nanotubes are open at both ends and capable of allowing mass transport from one side of the membrane to the other through the titania nanotubes by fluid flow.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins, wherein the amino acid residues are linked by covalent peptide bonds.

"Fluid contact" refers to a location of two or more entities relative to each other in a manner that allows for fluid-phase mass transport between the entities.

"Water-soluble gas" refers to a gas that has a solubility in water at a temperature of 37° C. and a pressure of 1 atmosphere that is greater than the solubility of air in water at a temperature of 37° C. and a pressure of 1 atmosphere. The equilibrium solubility of air (oxygen and nitrogen combined) in water under these conditions is about 22 mg/liter (22 µg/mL). A water soluble gas (or mixture of gases) has a solubility of more than 22 mg/liter such as 23, 24, 25, 26, 27, 28, 29, 30, 31, 32, 33, 34, 35, 36, 37, 38, 39, 40 or more than 40 mg/liter.

The term "distal" in reference to a medical device or part thereof generally refers to an orientation away from a medical user of the device and towards a subject or patient. The term "proximal" in reference to a medical device or part thereof generally refers to an orientation towards a medical user of the device and away from a subject or patient.

The term "biodegradable" refers to the ability of a polymeric substance to degrade into lower molecular weight species when introduced into a biological environment. Examples include biodegradable polymers such as poly (lactic-co-glycolic acid) (PLGA).

The term "soluble" refers to the ability of a substance to dissolve into a solvent such as a biological fluid, without degrading into lower molecular weight species. Examples include biocompatible polymers like polyethylene glycol and polyvinyl pyrrolidone.

EMBODIMENTS

The invention pertains to the field of implantable drug delivery devices having a reservoir containing a therapeutic agent, and having one or more membranes providing pathways for mass transport through fluid flow between the reservoir and an environment of the drug delivery device. In preferred embodiments the membranes are porous membranes. The membranes may be configured to provide sustained release of the therapeutic agent after implantation of the device in the body of a subject. In some embodiments the membrane is a microporous membrane. In some embodiments the membrane is a nanoporous membrane such as those described in U.S. Patent Application Pub. No. 2014/0371687, incorporated herein by reference.

For shelf-stability purposes (i.e., shelf-life), it is often preferred that the therapeutic agent in such devices is in a solid state during storage of the device. In order for release of the therapeutic agent to occur, fluids may need to be introduced into the reservoir to dissolve the therapeutic agent and enable its release through the porous membrane.

Embodiments of the invention include apparatuses, methods and means to promote uptake of fluids into the reservoir of an implantable drug delivery device. In some embodiments a drug delivery device is part of the embodiment. In certain instances, the apparatuses, methods and means enable implantation of a drug delivery device having a reservoir into a subject, wherein the reservoir has a pressure which is less than atmospheric pressure (sub-atmospheric i.e., reduced pressure), such as less than 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, less than 0.01 atmosphere (<0.01) or even less. In certain aspects, the reservoir has a pressure of 0.009, 0.008, 0.007, 0.006, 0.005, 0.004, 0.003, 0.002, 0.001 atm or even less. The reduced pressure promotes the uptake of interstitial fluid into the reservoir.

Embodiments of the invention promote uptake of fluids into a reservoir of an implantable drug delivery device through a porous membrane by creating a pressure differential between the reservoir in the device and a fluid-filled environment of the device. For instance, creation of a reduced pressure inside a reservoir of an implantable drug delivery device having a porous membrane combined with insertion of the device in a subcutaneous pocket may promote the uptake of biological fluids, such as interstitial fluid, through the membrane and into the reservoir.

It should be understood that in the absence of the pressure differential created by embodiments of the invention interstitial fluid will ultimately be absorbed into the drug delivery device, mostly by slow dissolution of air inside the device into the incoming interstitial fluid. However, the time required for such hydration may not be medically acceptable. Embodiments of the invention allow for the time required for hydration or rehydration to be brought within medically acceptable limits. Since those limits may differ from one application to another, the extent to fluid uptake needs to be accelerated may be application dependent. In particular, the delay of drug release from a second implant, inserted after explanation of a first, depleted or substantially depleted implant, a so-called "drug holiday," may determine the acceptability of the rate of hydration of a dosage form. For instance, for a drug with a wide therapeutic window, and an elimination half-life of 18 hours or more, a delay in release after implantation of a second dosage form of 2 days or more may be acceptable. For a drug with a narrow therapeutic window, and half-life of a few hours, a 12-24 hour delay may be the maximum acceptable range.

In general, embodiments of the invention provide substantial hydration and initiation of significant drug release within 48 hours of implantation of a device in a subject. Preferred embodiments provide substantial hydration and initiation of significant drug release within 36 hours of implantation of a device in a subject. More preferred embodiments provide substantial hydration and initiation of significant drug release within 24 hours of implantation of a device in a subject.

Most preferred embodiments provide substantial hydration and initiation of significant drug release within 12 hours of implantation of a device in a subject.

Some embodiments of the invention are suitable for introducing the drug delivery device into the body of a subject, as well as for creating a reduced pressure inside a reservoir of a drug delivery device.

Some embodiments of the invention comprise a housing. Functions of the housing may include holding other components of the invention together into an apparatus suitable for use, providing a handle for an user to hold and operate the apparatus, and the like. The housing may be constructed out of any suitable material, including polymers, ceramics, composites and combinations thereof. Oftentimes, for purposes of ease of manufacturing and cost reduction, the housing will comprise molded polymeric parts.

Some embodiments of the invention comprise a tubular outer member, such as a tubular insertion member or tubular implantation member, extending from the housing in a distal direction. In some embodiments the outer member is attached to the housing. In some embodiments, the outer member is a slideable member, at least partially slideably disposed within the housing. The outer member may be configured to hold an implantable drug delivery device. In some embodiments the insertion member or implantation member is a sharpened member, such as a hollow needle, suitable to penetrate the skin, to access areas within the body of a subject, such as the subcutaneous space, and deliver an implantable drug delivery device into the subcutaneous space. In some embodiments the tubular insertion member is a blunt member, suitable to access areas within the body of a subject after penetrating the skin with a separate implement, such as a scalpel. In some embodiments the separate implement is included in the embodiment. The tubular outer member may be constructed out of any suitable material. Preferred materials of construction include metals, polymers, ceramics, composites and combinations thereof. Examples of metals include stainless steel and titanium. Examples of polymers include polyethylene, polypropylene, polyurethanes, acrylonitrile butadiene styrene, polyether ether ketone, etc. In some embodiments, the tubular outer member is not used for insertion of an implant into the body of a patient, but to prepare an implant for implantation just before the actual insertion procedure.

Some embodiments comprise an obturator. Obturators of the invention may comprise elongated members, slideably disposed within a tubular outer member. In some embodiments the obtorators are slideable obturators. In some embodiments, the obdurators are attached to the housing, and the tubular outer member is slideable disposed around the obturator. Functions of the obturator include providing a means to an operator to move an implantable drug delivery device, disposed within the tubular outer member, with respect to the tubular outer member or to hold a drug delivery device, disposed within a tubular outer member stationary, while moving the tubular outer member. The obturator may be constructed out of any suitable material.

Preferred materials of construction include metals, polymers, ceramics, composites and combinations thereof. Examples of metals include stainless steel and titanium. Examples of polymers include polyethylene, polypropylene, polyurethanes, acrylonitrile butadiene styrene, polyether ether ketone, etc.

Some embodiments of the invention comprise a pressure reducer. In embodiments comprising a drug delivery device, the pressure reducer may be in fluid contact with the membrane of the drug delivery device. Some embodiments comprise a pressure reducer configured as a slideable elongated member. In some embodiments the pressure reducer is at least partially slideably disposed within the outer member. In some embodiments the obturator is a tubular obturator, and the pressure reducer is at least partially slideably disposed within the obturator. In some embodiments, the pressure reducer is a tubular pressure reducer, and the obturator is at least partially slideably disposed within the pressure reducer. In some embodiments, the obturator and the pressure reducer are at least partially slideably disposed within the outer member in a side-by-side configuration.

Some embodiments comprise a slideable pressure reducer outside the tubular outer member, for instance in a cavity in a housing, wherein the housing holds the outer member, the obturator and the pressure reducer.

Functions of the pressure reducer include providing a means to an operator to reduce the pressure inside a reservoir of an implantable drug delivery system to promote uptake of fluids into the reservoir. The pressure reducer may be constructed out of any suitable material.

Preferred materials of construction include metals, polymers, ceramics, composites and combinations thereof. Examples of metals include stainless steel and titanium. Examples of polymers include polyethylene, polypropylene, polyurethanes, acrylonitrile butadiene styrene, polyether ether ketone, etc.

Some embodiments include connectors for connecting to a separately supplied pressure reducer, such as a syringe or a vacuum pump.

As will be explained further below, in some embodiments, moving a slideable pressure reducer, disposed within a tubular outer member or within a cavity in a housing, from a distal to a proximal position inside the tubular outer member or the cavity in the housing creates a reduced pressure in the tubular outer member or the cavity in the housing, in a location distal to the pressure reducer and in fluid contact with a membrane of a drug delivery device contained within a tubular outer member.

In some embodiments, operating the pressure reducer reduces the pressure inside the tubular outer member or inside the cavity in the housing to less than 0.5 atmosphere. In preferred embodiments the pressure is reduced to less than 0.1 atmosphere. In most preferred embodiments, the pressure is reduced to less than 0.01 atmosphere.

Some embodiments of the invention include an implantable drug delivery device, slideably disposed within the tubular outer member. Drug delivery devices useable in the current invention comprise at least one reservoir containing a formulation of a therapeutic agent to be delivered from the device. Drug delivery devices of the invention further comprise at least one membrane to provide a pathway for delivery of the therapeutic agent out of the reservoir of the device and into an environment of use. In preferred embodiments the membrane is configured to control the release of the therapeutic agent for extended periods of time. In some preferred embodiments, release of the beneficial substance(s) is extended over at least one month. In more preferred embodiments, the release is extended over at least three months, 4, 5, 6, 7, 8, 9, 10, 11, or at least 12 months.

In some embodiments, a membrane controlling the rate of release of the therapeutic agent is a nanoporous membrane. In certain embodiments, there are two or more membranes in the device.

In some embodiments, the pores in the membranes are nanochannels, such as those disclosed in U.S. Pat. No. 8,480,637 incorporated herein by reference. In some embodiments, the pores in the membranes are nanotubes, such as those disclosed in U.S. Patent Application Pub. No. 2014/0371687 incorporated herein by reference.

In some embodiments, compositions of the invention are disposed within a reservoir of an extended-release dosage form controlled by a nanoporous membrane, wherein the nanoporous membrane is configured to achieve extended-release of the therapeutic agent from the reservoir of a device. In some embodiments, the release rate of the therapeutic agent is controlled by matching the dimensions of the pores in the nanoporous membrane to the molecular dimensions or the hydrodynamic dimensions of the therapeutic agent. In some embodiments, the smallest dimension of the pores is not more than 5 times a molecular dimension or hydrodynamic dimension of the therapeutic agent. In some embodiments, the smallest diameter of the pores is not more than 1, 2, 3, 4, 5, 6, 7, 8, 9, 10, 11, or 12 times a molecular dimension or hydrodynamic dimension of the therapeutic agent.

The drug delivery device may be held in place by any desired means, including means such as a precision fit inside the outer member with tolerances to provide adequate immobilization of the device or an adequate sealing function as described below, while still allowing for sufficient slideability of the device. In some embodiments the device or the outer member may have a slightly ovalized section to provide a friction fit to hold the device in place. Some embodiments of the invention include a separate drug delivery device, configured to be loaded into a tubular outer member prior to use. Some embodiments of the invention do not include a drug delivery device, and are configured to be loaded with a separately provided drug delivery device.

In some embodiments the drug delivery device contains a formulation of protein or peptide. Suitable peptides include, but are not limited to, beta-glucocerobrosidase, interferon alpha, interferon beta, interferon gamma, agasidase alpha, agasidase beta, exenatide, octreotide, LHRH, LHRH analogs, calcitonin, nutropin/somatropin, factor VIII, aldesleukin, forigerimod, NP fusion proteins, IL-12, a melanocyte stimulating hormone, and bapineuzumab. In some embodiments, the protein or peptide therapeutic agents are Glucagon-Like Peptide-1 receptor agonists also known as GLP-1 receptor agonists. In some embodiments, the GLP-1 receptor agonist is exenatide. In certain instances, exenatide has CAS No. 141732-76-5 and an empirical formula of $C_{184}H_{282}N_{50}O_{60}S$. In preferred embodiments, the amount of exenatide can be from about 60 μg to about 50 mg, such as 100 μg, 200 μg, 300 μg, 400 μg, 500 μg, 600 μg, 700 μg, 800 μg, 900 μg, 1 mg, 10 mg, 20 mg, 30 mg, 40 mg, or 50 mg.

Turning now to FIGS. 1-9, the structure and mode of operation of the invention will be illustrated by way of a number of exemplary embodiments. In the embodiment illustrated in FIG. 1, slideably disposed within tubular outer member 1001 are implantable drug delivery device 1002 having an internal reservoir as described above, and slideable tubular obturator 1003. Disposed within tubular obturator 1003 is slideable pressure reducer 1004. Porous membrane 1005 is located towards the proximal end of drug delivery device 1002. Located between the distal end of tubular obturator 1003 and the proximal end of drug delivery device 1002 is connector 1006. Connector(s) 1006 is configured to provide a sealing mechanism between the distal end of tubular obturator 1003 and the proximal end of drug delivery device 1002 to maintain a reduced pressure during operation of the embodiment. Connector(s) 1006 is attached to tubular obturator 1003, for instance by use of an adhesive, or, in the case of an O-ring or a washer by having a pressure fit inside a rim or groove provided along the outer perimeter of the distal end of obturator 1003, or by any other suitable means or combination of means. In some embodiments, the distal end of obturator 1003 itself forms a sealing mechanism with the proximal end of drug delivery device 1002. Pressure reducer 1004 and tubular obturator 1003 are manufactured with adequate precision that the interface between the inner surface of obturator 1003 and the outer surface of pressure reducer 1004 provides a sealing mechanism to maintain a reduced pressure during operation of the embodiment.

Figure 2:
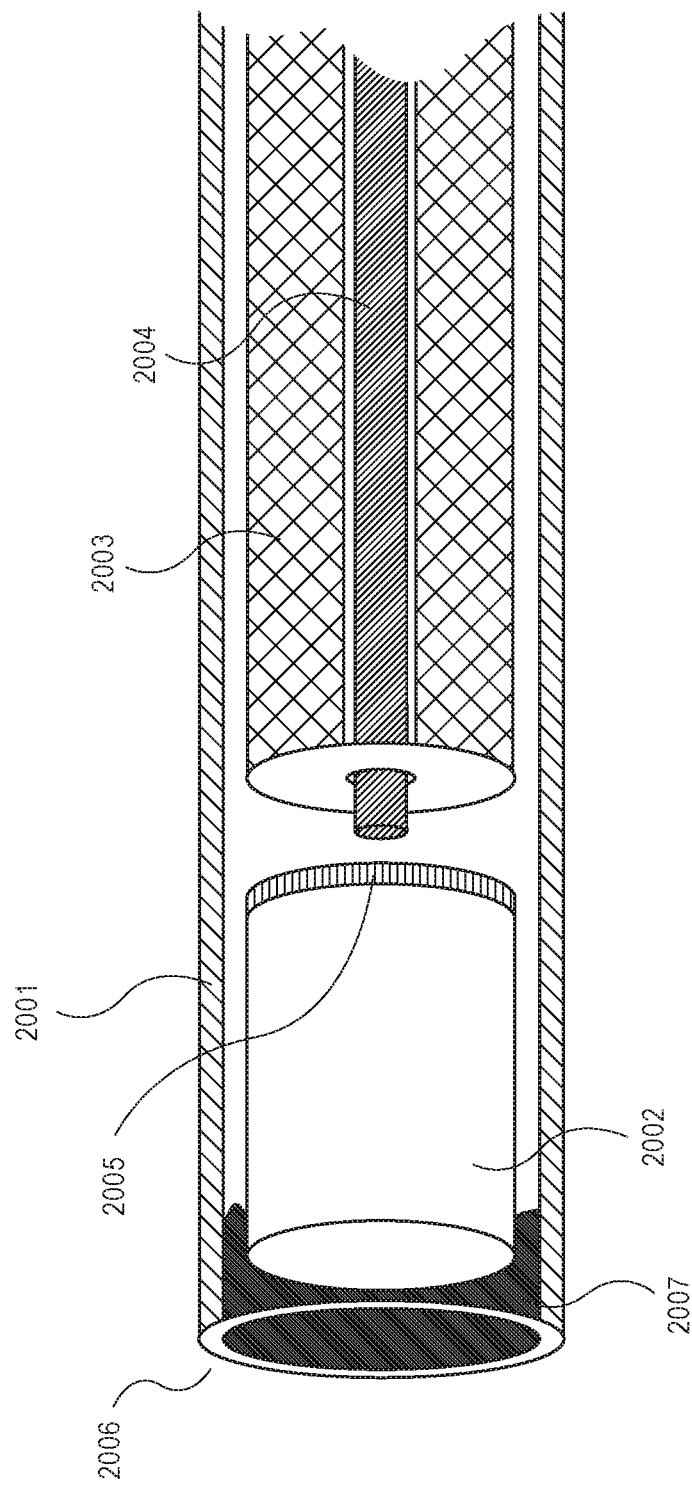
FIG. 2 illustrates a cross-sectional side view of an embodiment of the invention.

In an alternative embodiment, a sealing mechanism is provided by a plug disposed within an outer member, distal to an implantable drug delivery device. As illustrated in FIG. 2. slideably disposed within tubular outer member 2001 are implantable drug delivery device 2002 having an internal reservoir as described above, and slideable tubular pressure reducer 2003. Disposed within tubular pressure reducer 2003 is slideable obturator 2004. Porous membrane 2005 is located towards the proximal end of drug delivery device 2002. Located towards distal tip 2006 of tubular outer member 2001 is plug 2007. Plug 2007 is preferably a soluble or a biocompatible material. Similar plugs have been described in International Patent Application PCT/US15/63940, incorporated herein by reference. In some embodiments, plug 2007 may extend into the space between the wall of tubular outer member 2001 and implantable drug delivery device 2002. This may be the case, for instance, when plug 2007 is introduced into outer member 2001 in liquid form after placement of drug delivery device 2002, and allowed to penetrate the space between the wall of outer member 2001 and drug delivery device 2002, and to harden in place. In some embodiments, plug 2007 may act as a sealing mechanism. In some embodiments, the implantable drug delivery device and the tubular outer member may be manufactured with a precision that allows the drug delivery device itself to act as a plug and form a sealing mechanism.

Figure 3:
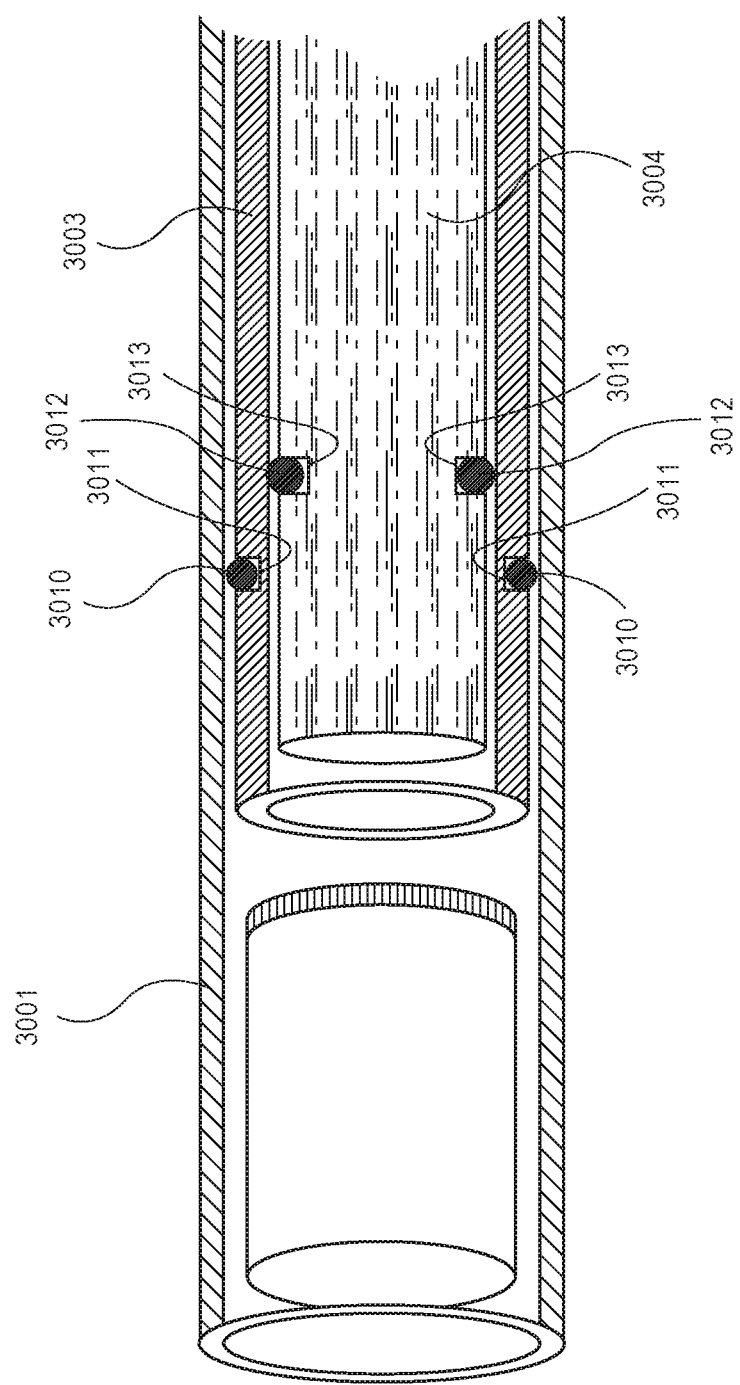
FIG. 3 illustrates a cross sectional side view of an embodiment of the invention using sealing mechanisms like O-rings.

As illustrated in FIG. 3, sealing mechanisms like gaskets, washers and O-rings may be incorporated between sliding members of the apparatus to provide improved sealing mechanisms. In FIG. 3, O-ring 3010 is located in a groove 3011 on tubular obturator 3003 inside outer member 3001, and O-ring 3012 is located in groove 3013 on sliding pressure reducer 3004. The invention does not put any a priori limitations on the locations or number of the seals, other than that a low pressure lumen can be created to reduce the pressure inside a reservoir of a drug delivery device. For instance, O-ring seals may be positioned between any two sliding surfaces of embodiments of the invention. Various sealing mechanisms and means, such as washer, gaskets, O-rings, precision fits and the like can be used interchangeably on embodiments of the invention, and those with ordinary skills in the art of mechanical engineering and medical device design will be able to determine the most suitable mechanisms based on such considerations as cost, quality, reliability, durability, sterilizability and the like.

The general function of some embodiments of the invention, and their method of use are illustrated in an exemplary embodiment in FIG. 4A-4C. In FIG. 4A, tubular outer member 4001 extends from housing 4007 in a distal direction, and is partially disposed within housing 4007 in a slideable manner. Tubular outer member 4001 is configured as a hollow needle with a sharpened distal tip 4014. Tubular obturator 4004 is disposed within outer member 4001 and within housing 4007, and is attached to housing 4007 though posts 4009. Slideable pressure reducer 4003 is partially disposed within obturator 4004. O-ring 4012 forms a sealing mechanism between obturator 4004 and outer member 4001, and O-ring 4013 forms a sealing mechanism between pressure reducer 4003 and obturator 4004. Implantable drug delivery device 4002 is located within outer member 4001 towards sharpened distal tip 4014. Plug 4006 seals the lumen of outer member 4001 distal to implantable drug delivery device 4002. Housing 4007 holds the various components of the apparatus, including outer member slider 4015 attached to outer member 4001.

During operation of the device an operator may insert outer member 4001 underneath the skin of a subject. As illustrated in FIG. 4B, the operator moves slideable pressure reducer in a proximal direction, creating a reduced pressure in lumen 4016 of tubular obturator 4004. Because of the sealing action of O-rings 4012 and 4013, and of plug 4006, the reduced pressure is propagated into the reservoir of drug delivery device 4002 through membrane 4005. In a next step, as illustrated in FIG. 4C, the operator may move outer member slider 4015, and, consequently, outer member 4001 in a proximal direction within housing 4007. By holding housing 4007, attached to obturator 4004 through posts 4009, stationary, obturator 4009 is held stationary under the skin. Consequently, drug delivery device 4002 and plug 4006 are held stationary under the skin, while outer member 4001 is withdrawn in a distal direction. Once drug delivery device 4002 is essentially expelled from the outer member, device 4002 is exposed to interstitial fluid, and the reduced pressure inside the reservoir may promote fluid uptake.

Figure 5:
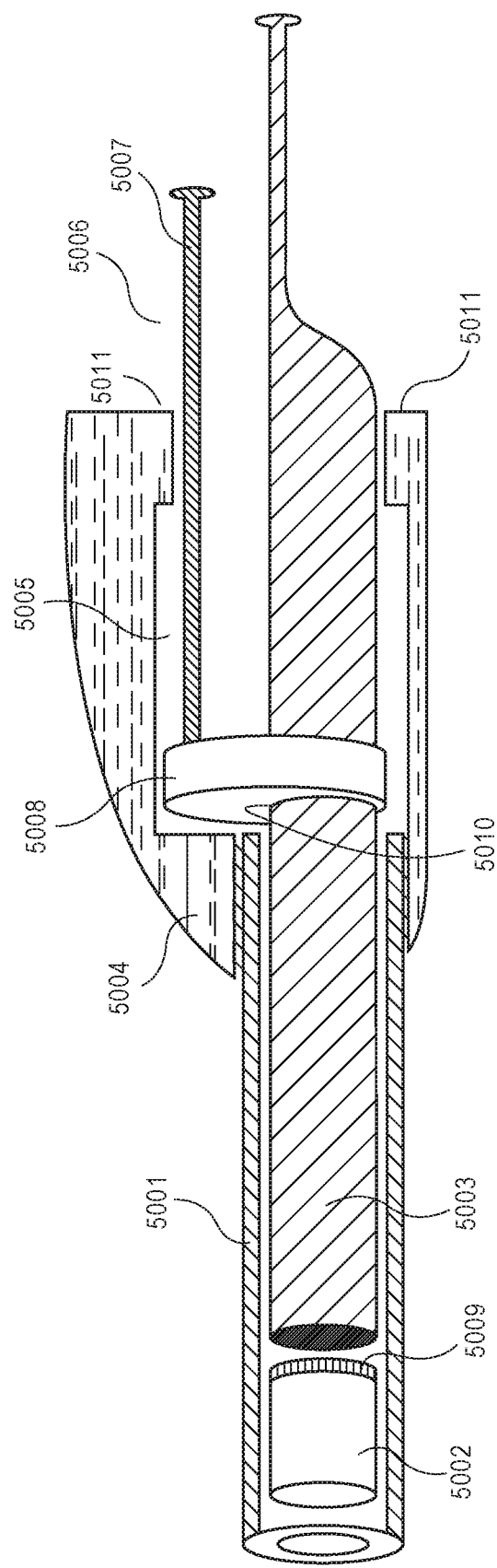
FIG. 5 illustrates a cross sectional side view of an embodiment of the invention.

Yet an alternative embodiment is illustrated in FIG. 5. Slideably disposed within tubular outer member 5001 are implantable drug delivery device 5002 having an internal reservoir as described above, and slideable obturator 5003. Outer member 5001 is attached to housing 5004. Implantable drug delivery device 5002 and outer member 5001 are machined with adequate precision that device 5002 forms a sealing mechanism within outer member 5001. In some embodiments, a sealing aid, such as a sealing fluid like a wax or a biocompatible oil may be used to improve the sealing mechanism. Housing 5004 holds outer member 5001 and obturator 5003. Housing 5004 has an internal cylindrical cavity 5005. Slideably disposed within cavity 5005 is plunger-shaped pressure reducer 5006, comprising handle 5007 and sealing disk 5008. Sealing disk 5008 forms a sealing mechanism with the wall of cavity 5005. Sealing disk 5008 has an aperture 5010, which forms a slideable seal around obturator 5003.

During use of the device a user may move pressure reducer 5006 from a distal to a proximal position until sealing disk 5008 abuts disk stops 5011, thereby creating reduced pressure inside the cavity section distal to sealing disk 5008, inside outer member 5001 and inside the reservoir of drug delivery device 5002 through membrane 5009. After insertion into the body of a subject, for instance in a subcutaneous space, the user may hold obturator 5003 stationary, and continue to move pressure reducer 5006 in a proximal direction. Since sealing disk 5008 abuts disk stops 5011, housing 5004 with attached outer member 5001 will move in a distal direction. Since obturator 5003 is held stationary, drug delivery device 5002 will essentially be expelled from outer member 5001 under the skin of the subject. Alternatively, pressure reducer 5006 may be immobilized against disk stops 5011, for instance by a including a ratchet mechanism on handle 5007 and disk stop 5011, allowing the user to use housing 5004 as a handle to move the housing, outer member 5001 and pressure reducer 5006 in a proximal direction.

Figure 6:
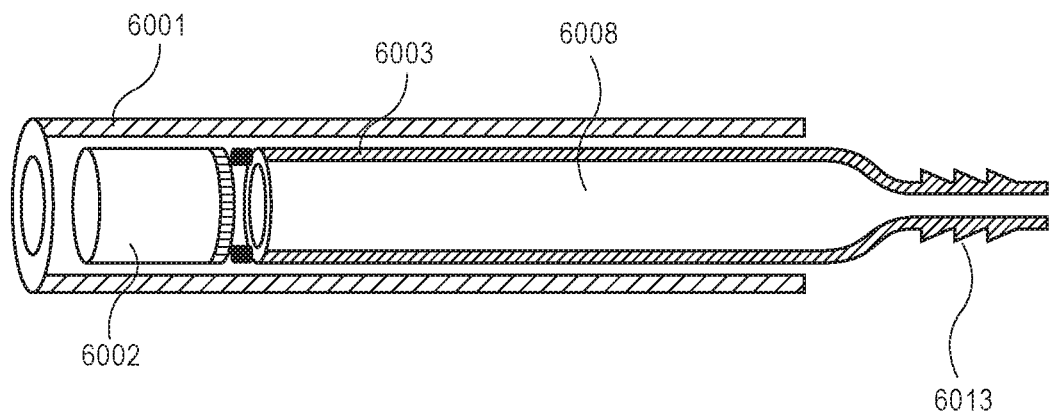
FIG. 6 illustrates a cross sectional side view of an embodiment of the invention.

In some embodiments an external pressure reducer may be employed in connection with embodiments of the invention. For instance, as shown in FIG. 6, slideable tubular obturator 6003 may be fitted with a connector 6013. Connector 6013 may be connected to an external pressure reducer, which may, for example be a vacuum pump, a vacuum line, or a syringe that can be used to create a reduced pressure in lumen 6008. Alternatively, outer member 6001 may be fitted with a connector to an external vacuum source, for instance in combination with a sealing plug inside hollow outer member 6001, distal to implantable drug delivery device 6002.

In addition to the exemplary embodiments described above, other features may be included to improve control and facilitate operation of the inventions, such as levers and gears to operate moving parts, spring-loaded mechanisms, battery-operated embodiments, ergonomic shaping of the housing or of a handle to be included, etc. Those with ordinary skills in the art of mechanical engineering or medical device design will be able to design such features within the scope of the present invention.

The potential effect of the pressure reduction to promote fluid uptake can be calculated and the actual effectiveness experimentally determined in straightforward procedures. Determination of the theoretical reduction in pressure can be performed from construction drawings of the apparatus. For instance, as illustrated in FIG. 4A-4C, lumen 4016 is significantly enlarged by moving pressure reducer 4003 from a distal position, as illustrated in FIG. 4A, to a proximal position as illustrated in FIG. 4B. As was stated above, various components of the invention may be fabricated with adequate precision to form sealing mechanisms, and various sealing mechanisms, such as O-rings, may be incorporated into the embodiments. In the case that these sealing mechanisms provide substantially hermetic seals, at least for the duration of the procedure to be performed by a medical professional, the resulting pressure reduction inside the embodiments can be calculated from the ratio of the sum of the volumes in the reservoir inside the drug delivery device and inside the void space in the tubular outer member before moving the pressure reducer, and the sum of the volumes in the reservoir inside the drug delivery device and inside the void space in the tubular outer member after moving the pressure reducer. Analogous calculations can be performed for other embodiments. Also, during the design phase of the embodiments, a pressure sensor can be introduced into volume 4016, or into the reservoir of drug delivery device 4002 to measure the actually achieved pressure reduction, and any decay in the reduction over time, due to potentially less than hermetic sealing by the various components. Experimentally, the adequacy of the pressure reduction can be determined by gravimetric measurement of fluid uptake into the reservoir of device 4002 after pressure reduction and exposure to fluids.

As described in International Patent Application PCT/US15/63940, incorporated herein by reference, it may be advantageous to include a water-soluble gas in implantable drug delivery devices, such as the ones in this disclosure, instead of air. As defined in International Patent Application PCT/US15/63940, the term "water-soluble gas" refers to a gas that has a higher solubility in water at 37° C. and 1 atmosphere than the solubility of air in water under those conditions. In such embodiments the water-soluble gas can act as a humectant, and attract water into the reservoir of the device to promote dissolution and release of the therapeutic agent. The concepts disclosed in PCT/US15/63940 can be advantageously combined with embodiments of the present invention. During manufacture of the apparatus air inside the reservoir of drug delivery device and in the interior lumens of the apparatus can be replaced with a water-soluble gas. Such embodiments have multiple advantages, including a combined action of reduced pressure and humectant activity of the water-soluble gas, as well as potentially improved shelf-stability of the product, since water-soluble gases like $CO_2$ are less reactive with drug substance than the oxygen in air.

Figure 7:
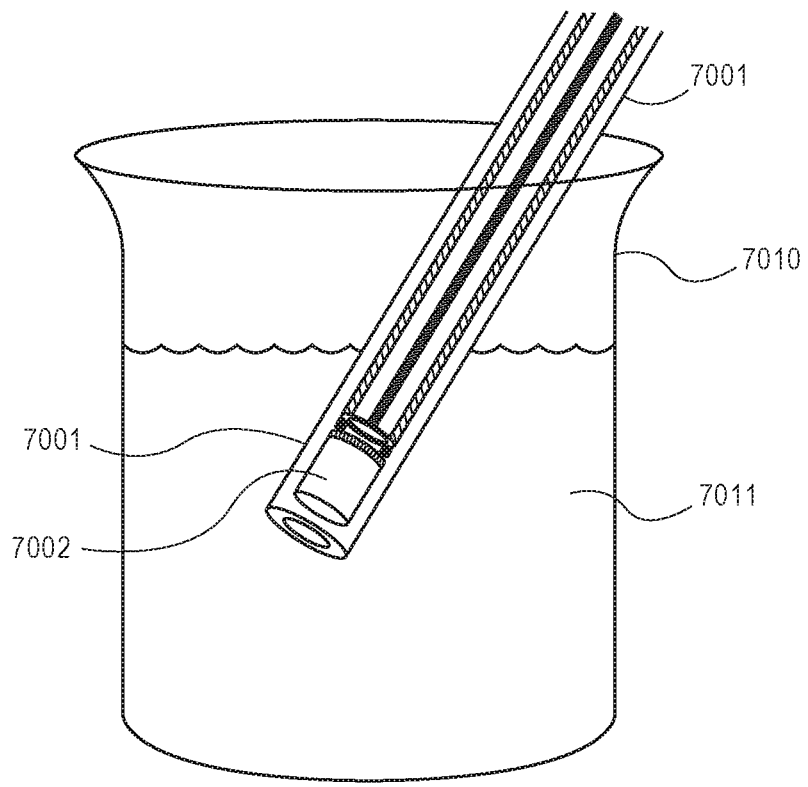
FIG. 7 illustrates a cross sectional side view of the use of an embodiment of the invention to hydrate a drug formulation in a reservoir of a drug delivery device.

As illustrated in FIG. 7, in an alternative embodiment of use of the invention, a user can perform essentially the same procedure to promote hydration, but rather than inserting the outer member into a subject, the user submerges the distal end of outer member 7001 in a container 7010 with a liquid 7011 such as a buffer used for uptake into the reservoir. After creating the reduced pressure, drug delivery device 7002 is expelled into liquid 7011. After sufficient time has passed for liquid uptake to occur, the device is retrieved from container 7010, and is ready to be implanted into a subject by any means deemed desirable by the user.

Figure 8:
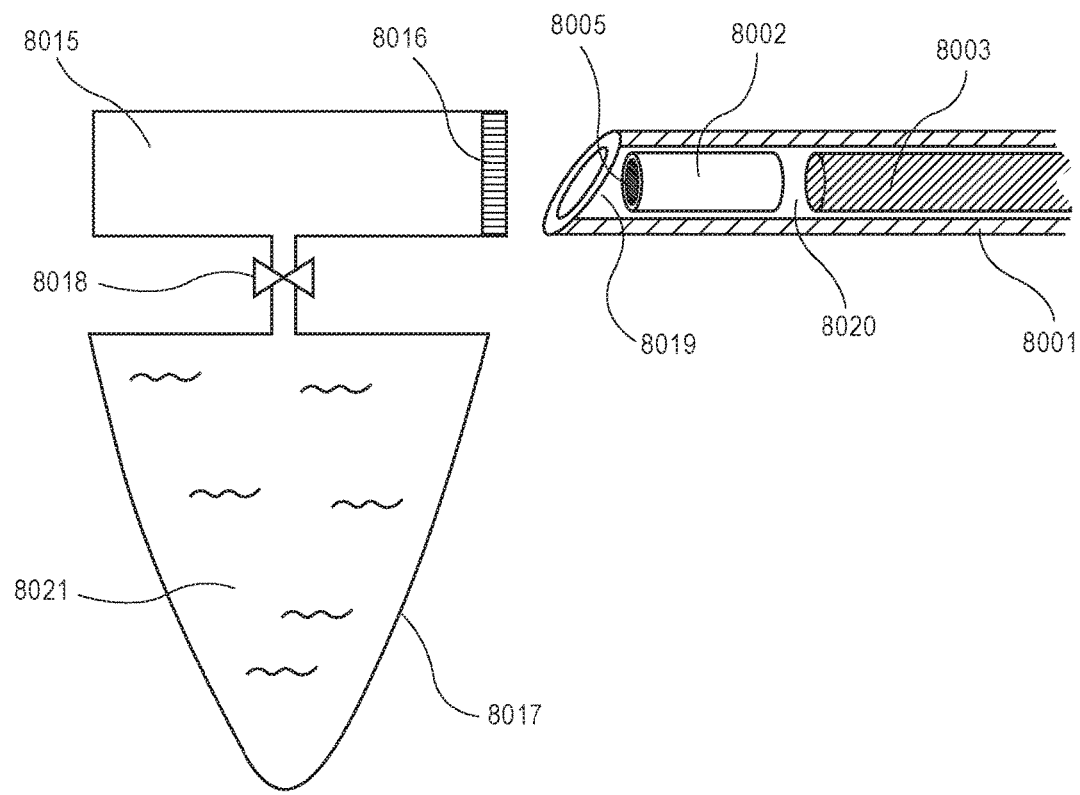
FIG. 8 illustrates a cross sectional side view of an embodiment of an accessory unit according to the invention.

Some embodiments of the invention comprise an accessory unit suitable for improving fluid uptake into a reservoir outside the body of a subject. FIG. 8 illustrates an embodiment of the invention having such an accessory unit. Chamber 8015 is fitted with septum 8016. Chamber 8015 may contain any suitable gas, such as air, $N_2O$ or $CO_2$, and may be at any desirable pressure. Chamber 8015 is connected with chamber 8017 by means of valved connector 8018. Drug delivery device 8002 and obturator 8003 are slideably disposed within tubular outer member 8001. Drug delivery device 8002 has a porous membrane 8005. Obturator 8003 and tubular outer member 8001 are machined such that a sealing mechanism is formed between the outer surface of obturator 8003 and the inner surface of tubular outer member 8001. In these embodiments, obturator 8003 may perform functions of a pressure reducer described in embodiments of FIGS. 1-7.

During use, a user inserts the sharpened tip of tubular outer member 8001 into chamber 8015 through septum 8016, and subsequently pulls obturator 8003 in a proximal direction to create a reduced pressure in spaces 8015, 8019 and 8020. The reduced pressure is propagated into the reservoir of drug delivery device 8002 through porous membrane 8005. Once a sufficiently reduced pressure has been achieved, the user opens valved connector 8018, to let fluid 8021 from chamber 8017 into chamber 8015.

In other embodiments the valved connector may be an automatic connector, responsive to reduced pressure in chamber 8015. In order to facilitate the fluid transfer, chamber 8017 may have a variable volume, for instance by manufacturing the wall of chamber 8017 from a flexible material. The reduced pressure in the reservoir of drug delivery device 8002 facilitates uptake of the fluid 8021 through membrane 8005.

Figure 9:
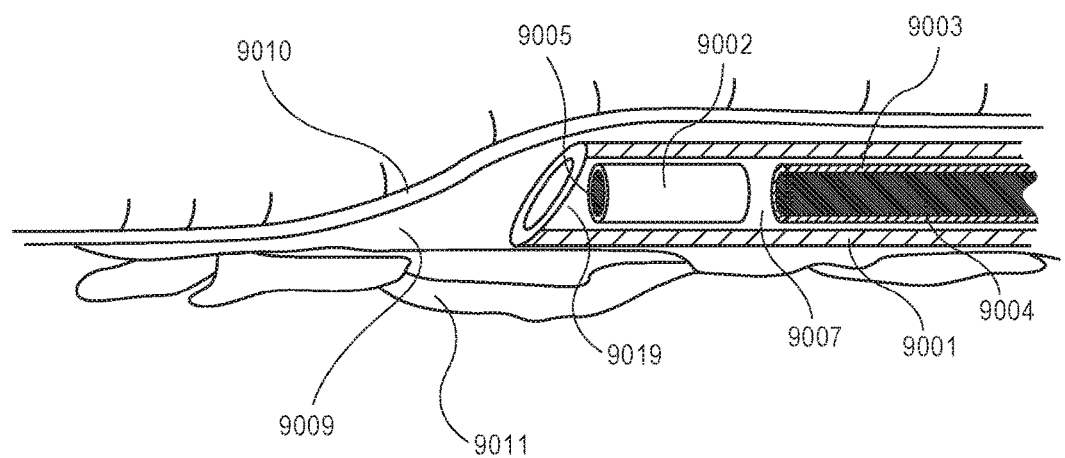
FIG. 9 illustrates a cross sectional side view of an embodiment of the invention inserted under the skin of a patient.

Some embodiments of the invention create a reduced pressure in the reservoir of a drug delivery device upon insertion of a tubular outer member into the body of a subject such as a human. As illustrated in FIG. 9, drug delivery device 9002 and tubular obturator 9004 are slideably disposed within tubular outer member 9001. Slideable pressure reducer 9003 is disposed within tubular obturator 9004. Drug delivery device 9002 has porous membrane 9005. During use, a user inserts the distal tip of tubular outer member 9001 into the body of a subject on a location outside of any major blood vessels, for instance in a subdermal space or pocket 9009 between skin 9010 and underlying tissue 9011. In such locations the tissue pocket may provide a sealing mechanisms over the tip of outer member 9001. By pulling pressure reducer 9003 in a proximal direction, a reduced pressure is created in lumen 9007 of tubular outer member 9001, and propagated into the reservoir of drug delivery device 9002. After sufficient time has elapsed to allow reduced pressure to develop in the reservoir through porous membrane 9005, drug delivery device 9002 is expelled into subcutaneous tissue pocket by withdrawing outer member 9001 in a proximal direction, while holding obturator 9004 stationary.

EXAMPLES

Example 1

9 devices with 39 microliter titanium reservoirs were sealed with titanium screw caps holding nanoporous membranes as described in U.S. Patent Application Pub. No. 2014/0371687.

The devices were inserted in a stainless steel outer member with a volume of about 0.8 ml. The outer member was sealed with a plug at the distal end and attached to a 60 cc syringe at the proximal end. Reduced pressure was applied by moving the syringe plunger proximally, resulting in a pressure reduction to about 0.013 atm.

Figure 10:
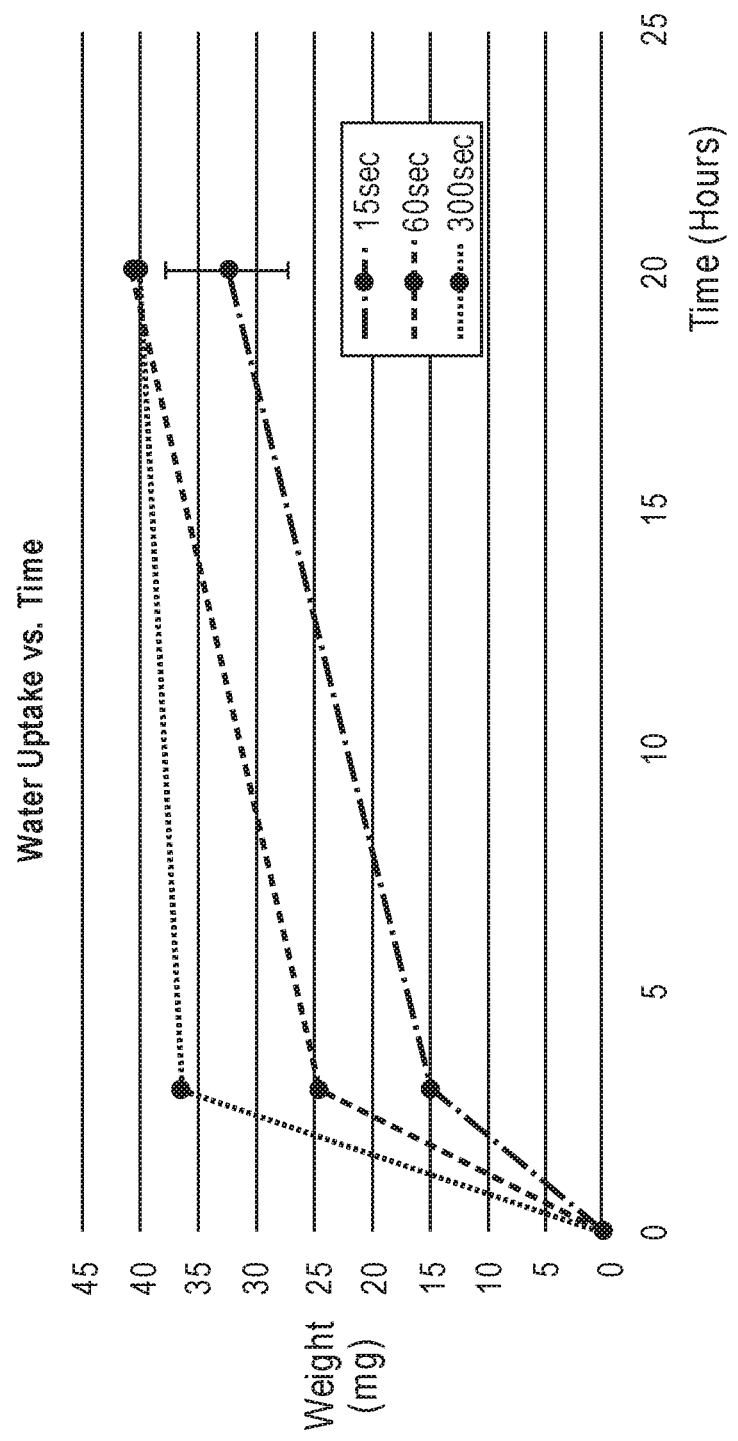
FIG. 10 is a graph showing weight gain as a function of time after hydration.

The devices were distributed in 3 groups, and reduced pressure was held for 15 seconds, 1 minute or 5 minutes for the individual groups. After the allotted time was elapsed, the tips of the outer members were submerged in water, and the devices expelled from the outer members. Water uptake was measured gravimetrically at 3 hours for 1 device in each group, and for all devices at 20 hours. The results are depicted in FIG. 10.

Example 2

7 devices with 39 microliter titanium reservoirs were filled with 13-18 mg of a dry powder formulation of exenatide. The reservoirs were sealed with titanium screw caps holding nanoporous membranes as described in U.S. Patent Application Pub. No. 2014/0371687. Initial weights of the powder-filled devices were recorded.

3 devices were submerged in phosphate buffered saline pH 7.4 (PBS) at 37° C. at atmospheric pressure in HPLC vials, without further pretreatment. 4 devices were subjected to a pressure reduction by introducing them into a vacuum chamber and reducing the pressure in the chamber to 0.03 atm. The devices were submerged in PBS at 37° C. by introducing the PBS into the vacuum chamber, after which they were transferred to individual HPLC vials and incubated at 37° C. The weight increases and exenatide release of the devices were followed over time. Weights were corrected for 11 mg of "outside" PBS caught in the threads and other features of the devices, as determined in a separate experiment.

Figure 11:
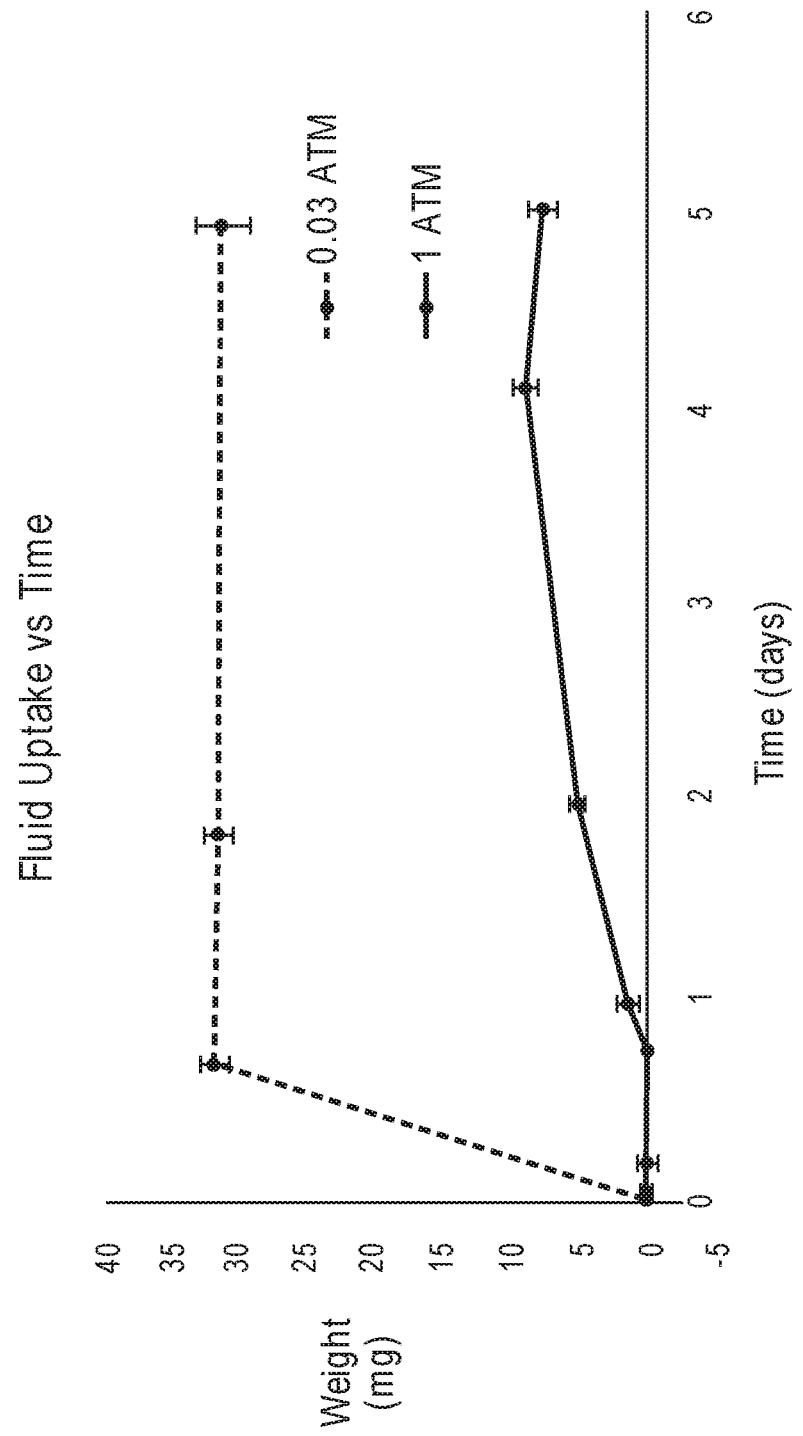
FIG. 11 is a graph showing fluid uptake over time.

FIG. 11 shows the difference in the average rate of PBS uptake between the two groups. Release rates were measured by performing HPLC on the incubation solutions. The incubation solutions were refreshed at regular intervals to avoid complications due to excessive degradation of exenatide in the buffer.

Figure 12:
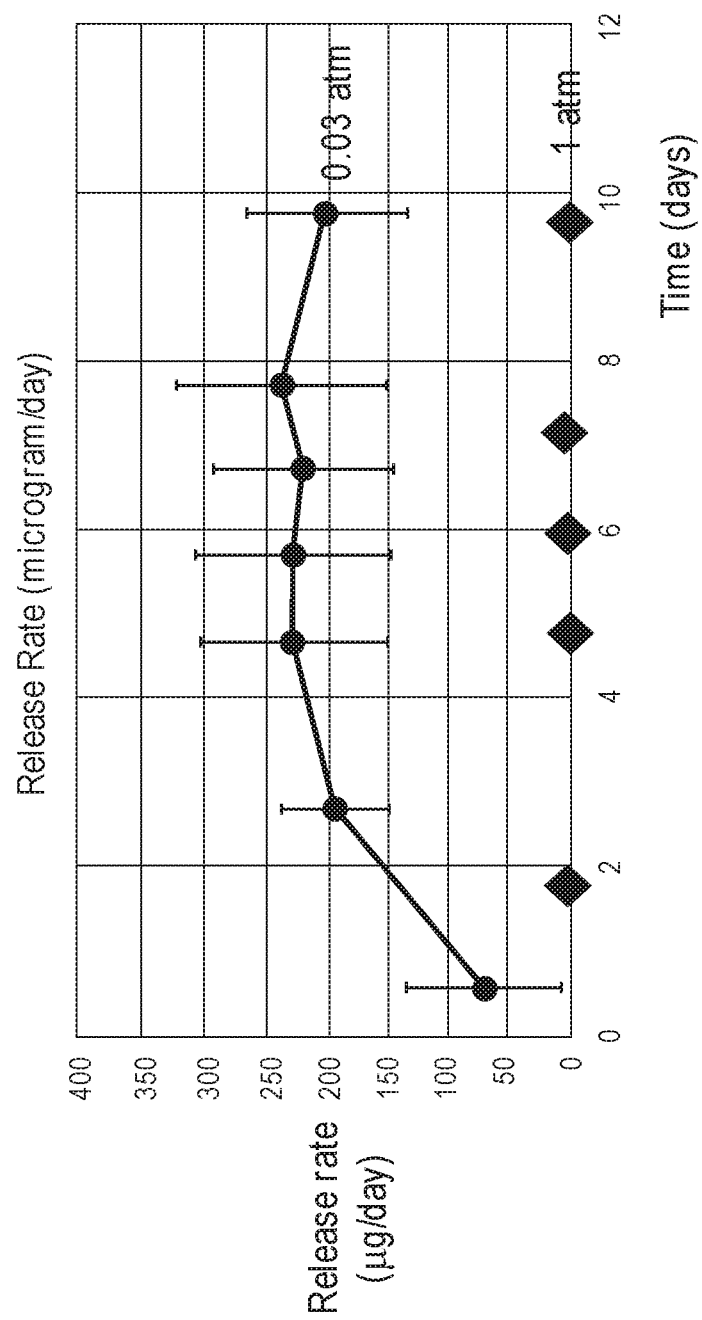
FIG. 12 is a graph showing drug release over time as a function of atmospheric pressure.

The results are shown in FIG. 12. No release of exenatide was detected in any of the vials without a vacuum pretreatment. The vacuum treated devices showed drug release as of the first day.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An apparatus for promoting fluid uptake into an implantable drug delivery device, the apparatus comprising:
   a housing;
   a tubular outer member, at least partially slidably disposed within the housing and having an affixed slider to slide the tubular outer member with respect to the housing, wherein the implantable drug delivery device is at least partially slidably disposed within the tubular outer member;
   an obturator, at least partially slidably disposed within the tubular outer member and located proximal to the implantable drug delivery device; and
   a pressure reducer configured to reduce the pressure inside a reservoir of the implantable drug delivery device containing a porous membrane and to promote uptake of fluids into the reservoir; wherein
   the membrane of the implantable drug delivery device provides a pathway for mass transport through fluid flow between the reservoir and an environement of the implantable drug delivery device; and wherein
   the porous membrane is in fluid contact with the pressure reducer.

2. The apparatus of claim 1, wherein the pressure reducer is a slideable pressure reducer.

3. The apparatus of claim 2, wherein the pressure reducer is at least partially disposed within the tubular outer member.

4. The apparatus of claim 2, wherein the obturator is tubular, and wherein the slideable pressure reducer is at least partially disposed within the tubular obturator.

5. The apparatus of claim 2, wherein the pressure reducer is tubular, and wherein the obturator is at least partially disposed within the tubular pressure reducer.

6. The apparatus of claim 1, wherein the tubular outer member is attached to the housing.

7. The apparatus of claim 1, wherein the tubular outer member is a slideable member, partially disposed within the housing.

8. The apparatus of claim 7, wherein the obturator is attached to the housing.

9. The apparatus of claim 1, further comprising:
   a cylindrical cavity having an inner wall, the cavity being located within the housing and being connected with the tubular outer member;
   wherein the slideable pressure reducer is at least partially disposed within the cylindrical cavity and comprises:
      a slideable cylindrical sealing plug in sealing contact with the inner wall of the cylindrical cavity;
      a handle, attached to the sealing plug and extending through the cylindrical cavity in a proximal direction; and
      an aperture in the sealing plug, the obturator being disposed through the aperture, the aperture forming a sealing mechanism around the obturator.

10. The apparatus of claim 1, wherein the porous membrane is a nanoporous membrane.

11. The apparatus of claim 1, wherein the porous membrane is a titania nanotube membrane.

12. The apparatus of claim 1, further comprising a plug, disposed within the tubular outer member in a location distal to the implantable drug delivery device, the plug providing a sealing mechanism within the tubular outer member.

13. The apparatus of claim 12, wherein the plug is a soluble plug.

14. The apparatus of claim 12, wherein the plug is a biodegradable plug.

15. The apparatus of claim 1, further comprising a quantity of gas disposed within the tubular outer member, wherein the quantity of gas includes at least 10% by weight of one or more gases with a solubility in water at a temperature of 37° C. and a pressure of 1 atmosphere that is higher than the solubility of air in water at a temperature of 37° C. and a pressure of 1 atmosphere.

16. An apparatus for promoting fluid uptake into an implantable drug delivery device, the apparatus comprising:
   a housing with a distal end and a proximal end;
   a tubular outer member with a distal end and a proximal end, the tubular outer member being attached to the housing towards the distal end of the housing and having an affixed slider to slide the tubular outer member with respect to the housing, wherein the implantable drug delivery device is at least partially slidably disposed within the tubular outer member;

a slideable obturator, at least partially disposed within the tubular outer member and located proximal to the implantable drug delivery device; and a pressure reducer configured to reduce the pressure inside a reservoir of the implantable drug delivery device containing a membrane and to promote uptake of fluids into the reservoir.

17. A method for promoting fluid uptake into an implantable drug delivery device, the method comprising:

providing an apparatus according to claim 1;

operating the pressure reducer to reduce pressure inside the reservoir;

introducing the implantable drug delivery device from the outer member into an environment containing a fluid; and exposing the reservoir through the membrane to the fluid.

18. An apparatus for promoting fluid uptake into an implantable drug delivery device, the apparatus comprising:

a housing with a distal end and a proximal end;

a tubular outer member with a distal end and a proximal end, the tubular outer member being attached to the housing towards the distal end of the housing and having an affixed slider to move the tubular outer member with respect to the housing, wherein the implantable drug delivery device is at least partially slidably disposed within the tubular outer member;

a slideable obturator, at least partially disposed within the tubular outer member and located proximal to the implantable drug delivery device; and a connector for connecting to a pressure reducer, wherein the pressure reducer is configured to reduce the pressure inside a reservoir of the implantable drug delivery device containing a membrane and to promote uptake of fluids into the reservoir.

* * * * *